(12) United States Patent
Martin (10) Patent No.: US 11,925,719 B1
(45) Date of Patent: Mar. 12, 2024

(54) SELF-SANITIZING DOOR KNOB SYSTEM

(71) Applicant: Raheem Martin, Brooklyn, NY (US)

(72) Inventor: Raheem Martin, Brooklyn, NY (US)

( * ) Notice: Subject to any disclaimer, the term of this patent is extended or adjusted under 35 U.S.C. 154(b) by 595 days.

(21) Appl. No.: 17/164,909

(22) Filed: Feb. 2, 2021

(51) Int. Cl.
*A61L 2/24* (2006.01)
*A61L 2/22* (2006.01)
*E05B 1/00* (2006.01)

(52) U.S. Cl.
CPC ............ *A61L 2/24* (2013.01); *A61L 2/22* (2013.01); *E05B 1/0069* (2013.01); *A61L 2202/14* (2013.01); *A61L 2202/15* (2013.01)

(58) Field of Classification Search
CPC . A61L 2/00; A61L 2/16; A61L 2/2224; A61L 2202/00; A61L 2202/10; A61L 2202/14; A61L 2202/15; E05B 1/00; E05B 1/0069
See application file for complete search history.

(56) References Cited

U.S. PATENT DOCUMENTS

| | | | |
|---|---|---|---|
| 6,874,697 B2 * | 4/2005 | Callueng | E05B 1/0069 239/69 |
| 7,338,646 B2 * | 3/2008 | Gilbert | A61L 2/18 422/292 |
| 7,360,674 B2 | 4/2008 | Sassoon | |
| 8,343,434 B2 | 1/2013 | Hyde | |
| 10,060,156 B1 | 8/2018 | Shack | |
| 10,487,537 B2 | 11/2019 | Cunningham | |
| 2013/0264355 A1 | 10/2013 | Jodoin | |

FOREIGN PATENT DOCUMENTS

| | | | |
|---|---|---|---|
| WO | 2004012778 | 2/2004 | |
| WO | WO-2019081006 A1 * | 5/2019 | ............... A61L 2/22 |

* cited by examiner

*Primary Examiner* — Natasha E Young
(74) *Attorney, Agent, or Firm* — Kyle A. Fletcher, Esq.

(57) ABSTRACT

The self-sanitizing door knob system is configured for use with a door. The door further comprises a door knob. The door knob is a manually operated mechanism that latches the door in a closed position. The door knob is a rotating structure that releases the latch to allow the door to rotate to an open position. The self-sanitizing door knob system is incorporated into the door knob. The self-sanitizing door knob system comprises a housing, a spray structure, and a control circuit. The housing contains the spray structure and the control circuit. The spray structure disinfects the door knob by discharging a spray disinfecting solution onto the door knob. The control circuit controls the operation of the spray structure.

18 Claims, 6 Drawing Sheets

SELF-SANITIZING DOOR KNOB SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of fixed construction including locks and door fittings, more specifically, sanitary doorknobs or handles comprising a disinfectant. (E05B1/0069)

SUMMARY OF INVENTION

The self-sanitizing door knob system is configured for use with a door. The door further comprises a door knob. The door knob is a manually operated mechanism that latches the door in a closed position. The door knob is a rotating structure that releases the latch to allow the door to rotate to an open position. The self-sanitizing door knob system is incorporated into the door knob. The self-sanitizing door knob system comprises a housing, a spray structure, and a control circuit. The housing contains the spray structure and the control circuit. The spray structure disinfects the door knob by discharging a spray disinfecting solution onto the door knob. The control circuit controls the operation of the spray structure. The control circuit: a) detects motion in the vicinity of the self-sanitizing door knob system; and, b) discharges the disinfecting solution onto the door knob when this motion is detected.

These together with additional objects, features and advantages of the self-sanitizing door knob system will be readily apparent to those of ordinary skill in the art upon reading the following detailed description of the presently preferred, but nonetheless illustrative, embodiments when taken in conjunction with the accompanying drawings.

In this respect, before explaining the current embodiments of the self-sanitizing door knob system in detail, it is to be understood that the self-sanitizing door knob system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the self-sanitizing door knob system.

It is therefore important that the claims be regarded as including such equivalent construction insofar as they do not depart from the spirit and scope of the self-sanitizing door knob system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
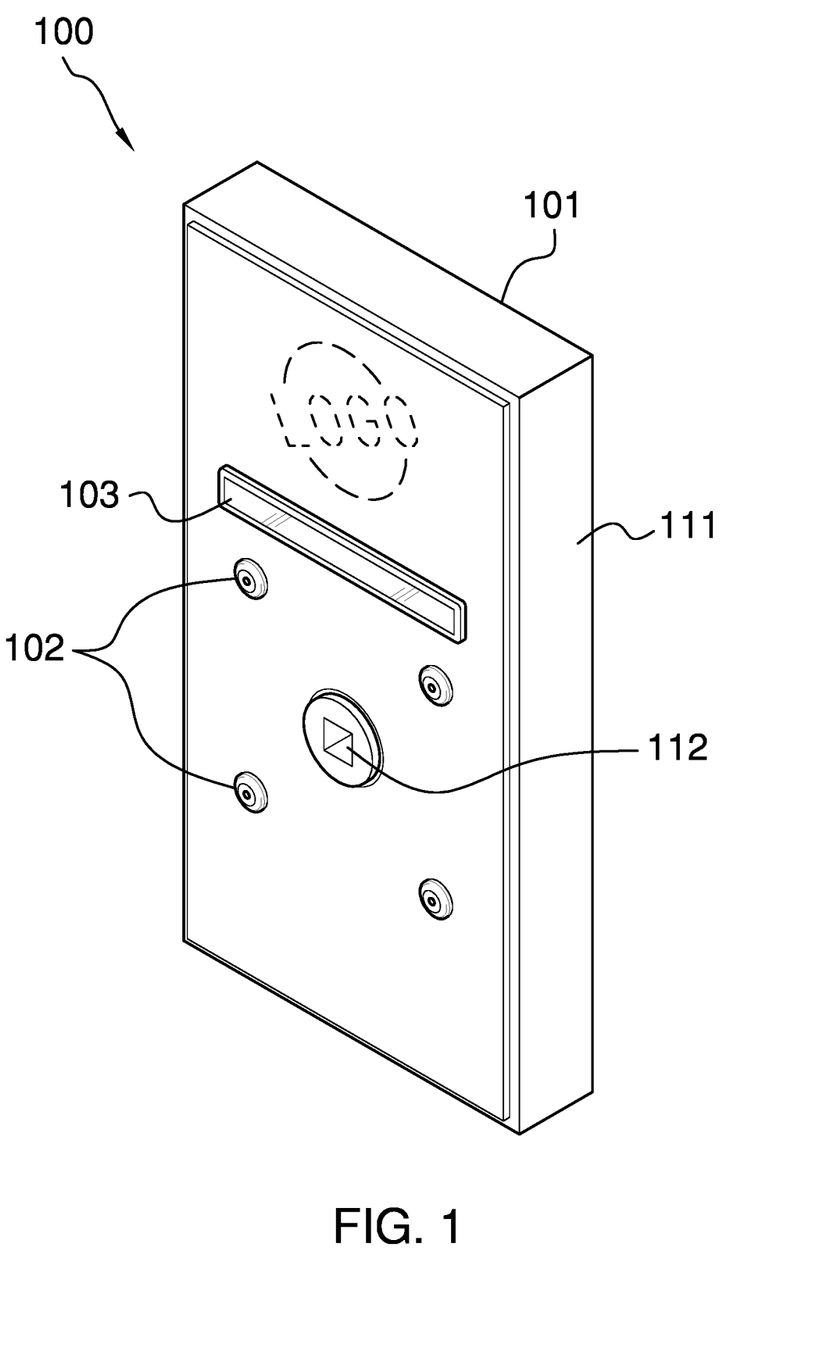
FIG. 1 is a perspective view of an embodiment of the disclosure.
Figure 2:
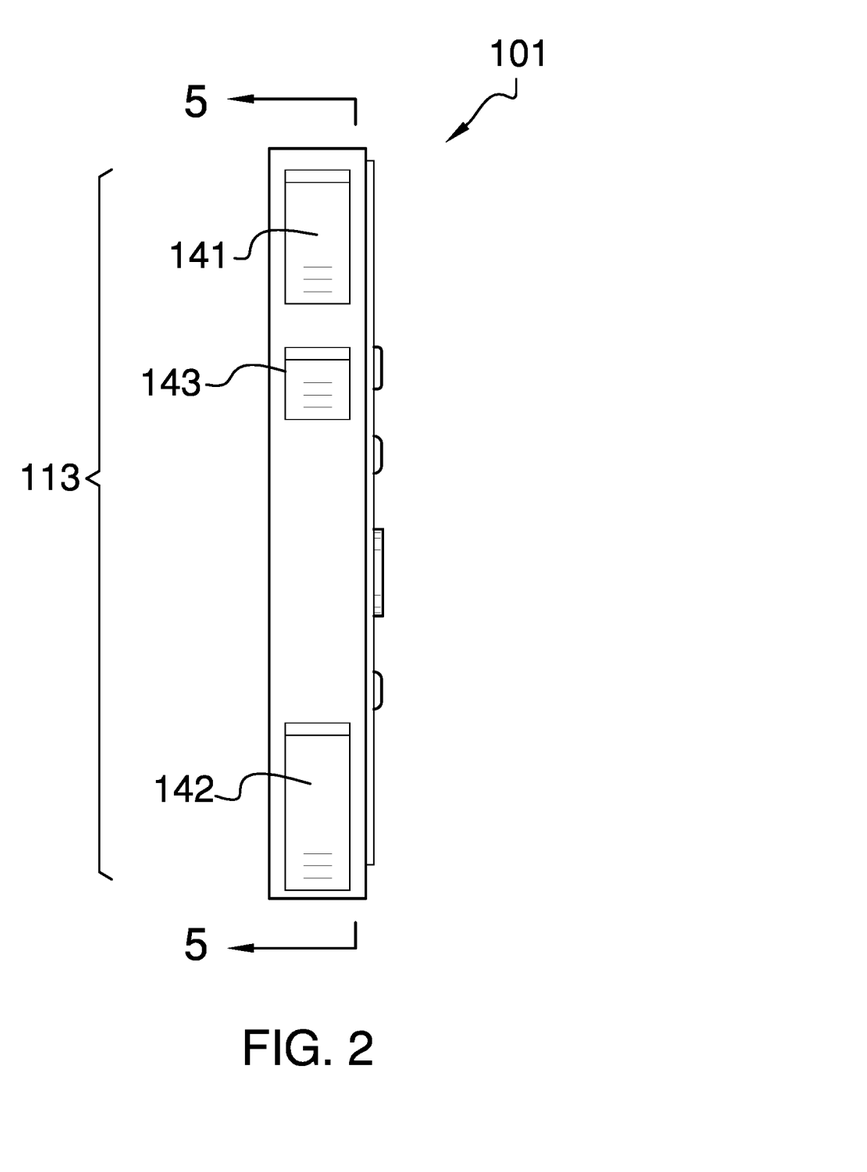
FIG. 2 is a side view of an embodiment of the disclosure.
Figure 3:
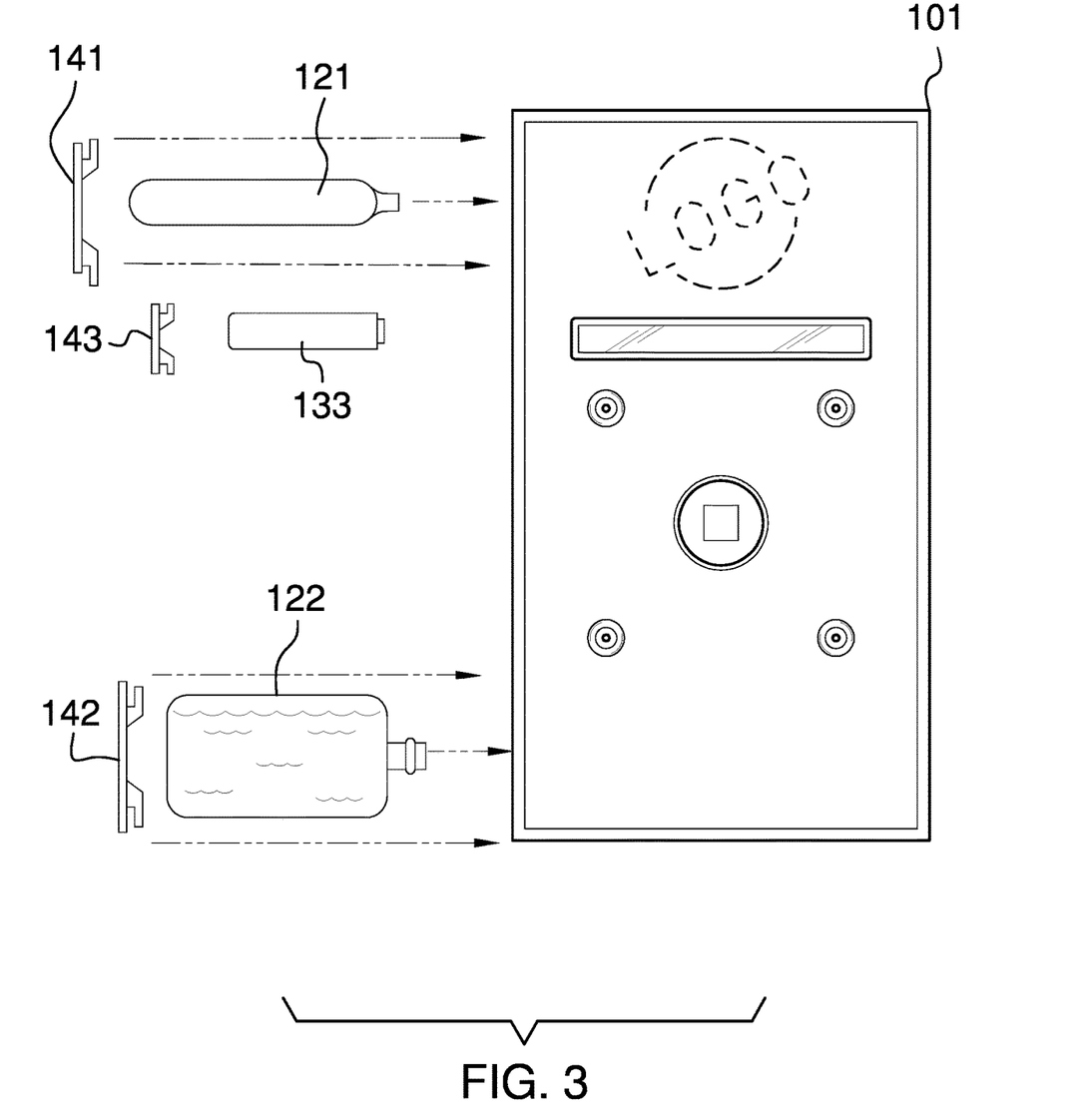
FIG. 3 is a front view of an embodiment of the disclosure.
Figure 4:
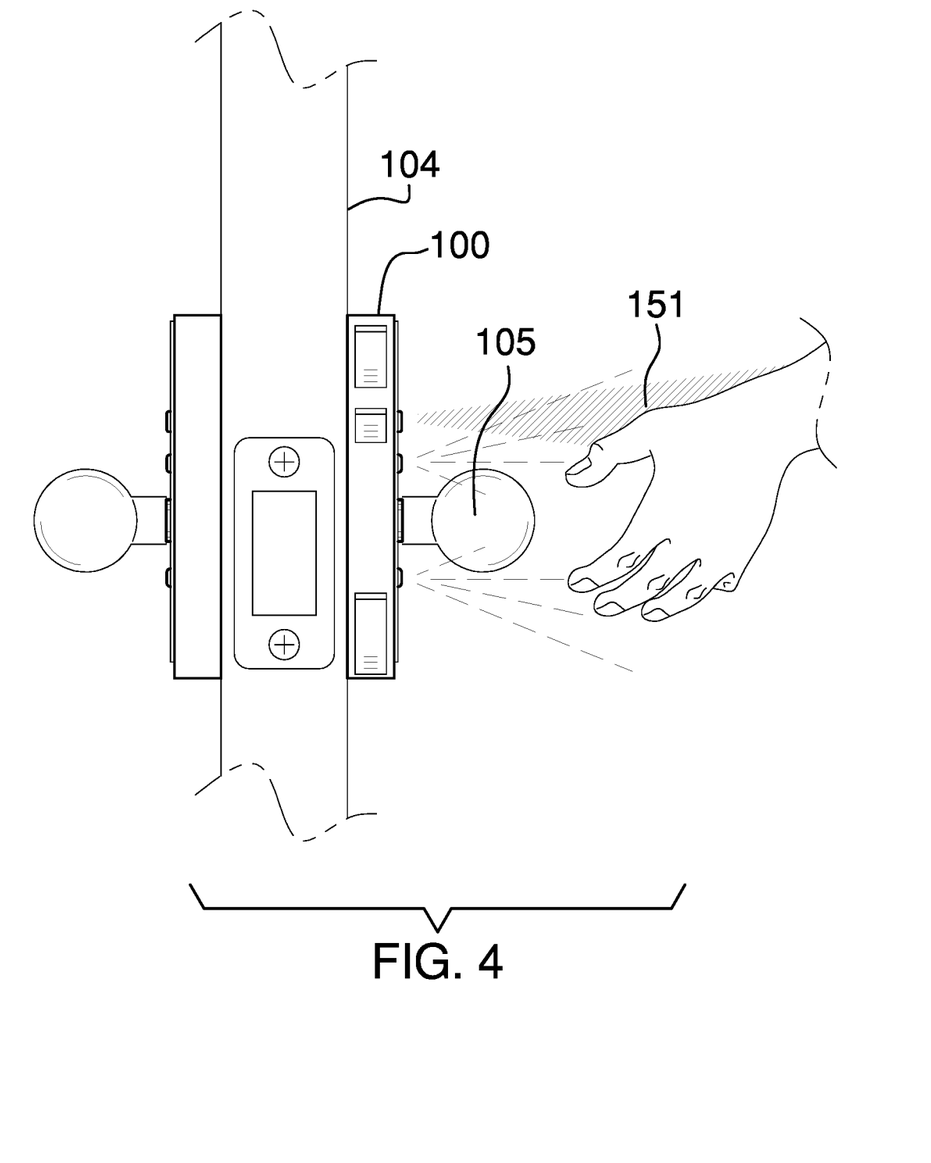
FIG. 4 is an in-use view of an embodiment of the disclosure.
Figure 5:
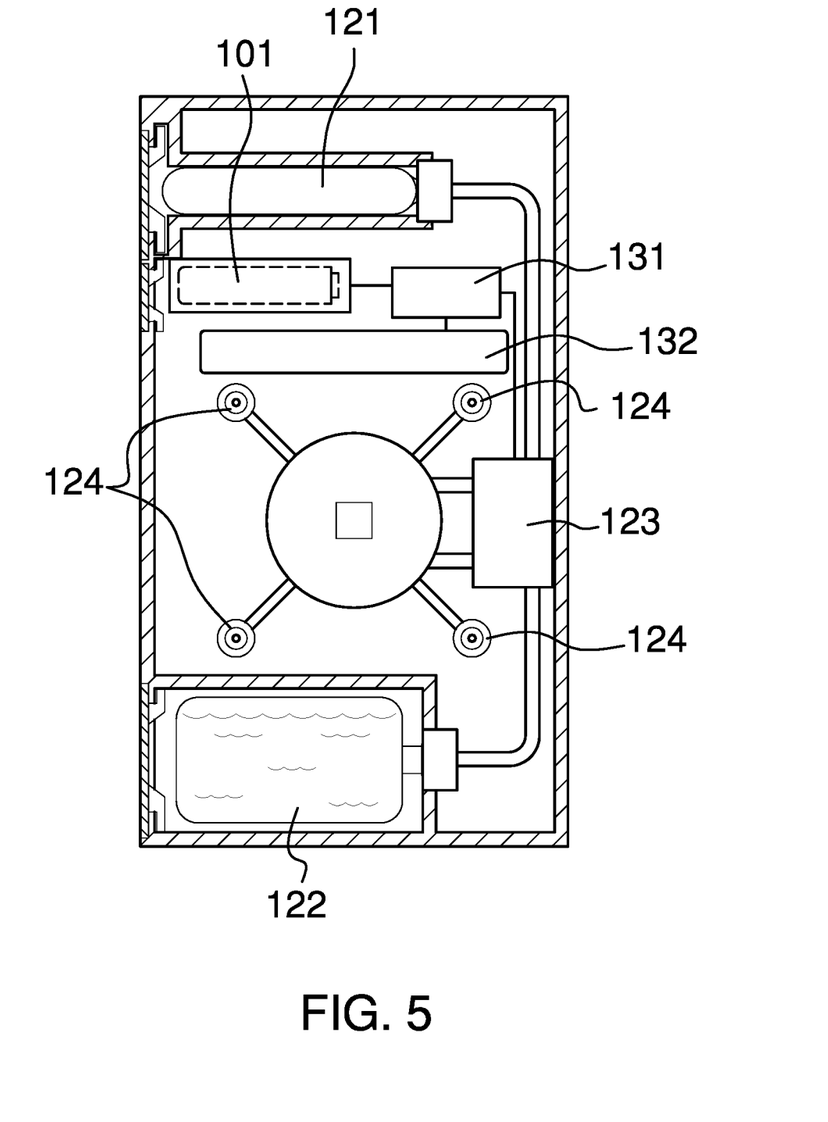
FIG. 5 is a cross-sectional view of an embodiment of the disclosure across 5-5 as shown in FIG. 2.
Figure 6:
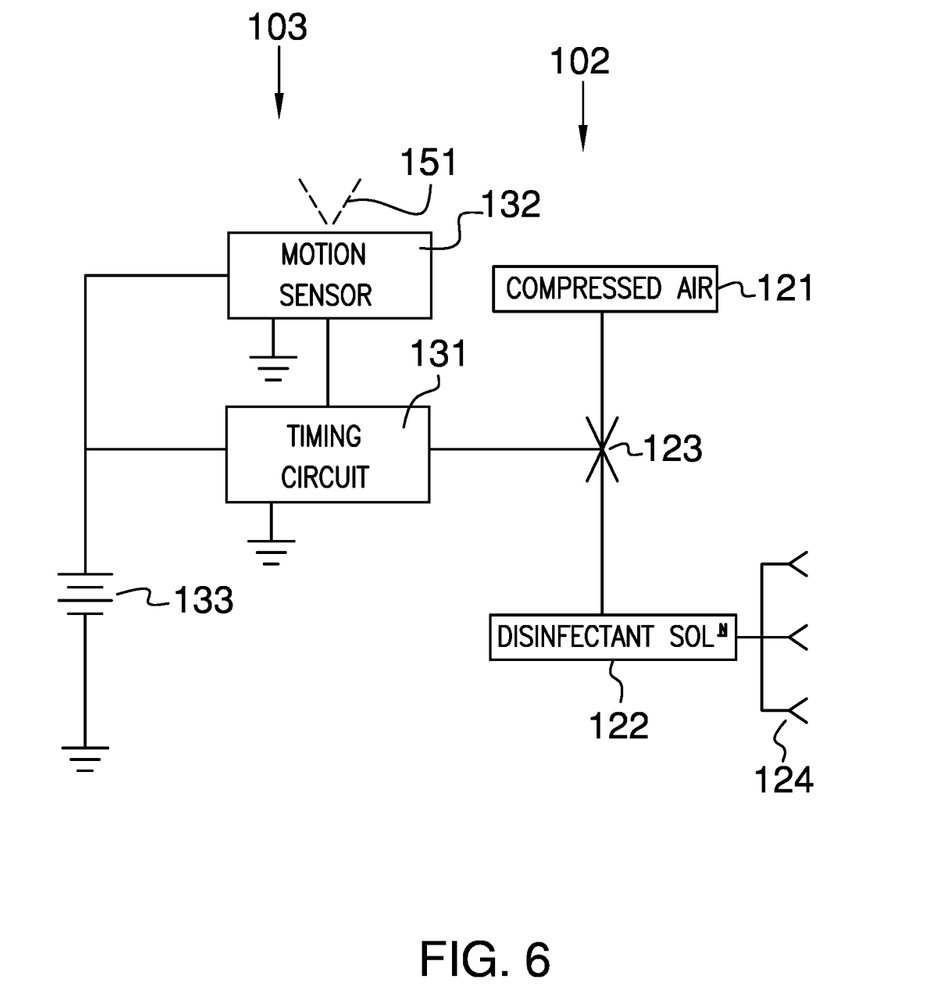
FIG. 6 is a schematic view of an embodiment of the disclosure.

Detailed reference will now be made to one or more potential embodiments of the disclosure, which are illustrated in FIGS. 1 through 6.

The self-sanitizing door knob system 100 (hereinafter invention) is configured for use with a door 104. The door 104 is defined elsewhere in this disclosure. The door 104 further comprises a door 104 knob 105. The door 104 knob 105 is a manually operated mechanism that latches the door 104 in a closed position. The door 104 knob 105 is a rotating structure that releases the latch to allow the door 104 to rotate to an open position.

The invention 100 is incorporated into the door 104 knob 105. The invention 100 comprises a housing 101, a spray structure 102, and a control circuit 103. The housing 101 contains the spray structure 102 and the control circuit 103. The spray structure 102 disinfects the door 104 knob 105 by discharging a spray disinfecting solution onto the door 104 knob 105. The control circuit 103 controls the operation of the spray structure 102. The control circuit 103: a) detects motion in the vicinity of the invention 100; and, b) discharges the disinfecting solution onto the door 104 knob 105 when this motion is detected.

The housing 101 is a rigid structure. The housing 101 contains the spray structure 102 and the control circuit 103. The housing 101 is formed with all apertures and form factors necessary to allow the housing 101 to accommodate the use and operation of the spray structure 102 and the control circuit 103. Methods to form a housing 101 suitable for the purposes described in this disclosure are well-known and documented in the mechanical arts. The housing 101 comprises a shell 111, an attachment structure 112, and a plurality of access doors 113.

The shell 111 is a prism-shaped structure. The shell 111 is formed as a disk. The shell 111 is a rigid structure. The shell 111 contains the spray structure 102 and the control circuit 103. The shell 111 is formed with all apertures and form factors necessary to allow the shell 111 to accommodate the use and operation of the spray structure 102 and the control circuit 103. Methods to form a shell 111 suitable for the purposes described in this disclosure are well-known and documented in the mechanical arts.

The attachment structure 112 is a mechanical structure. The attachment structure 112 attaches the shell 111 to the door 104 knob 105. The attachment of the attachment structure 112 to the shell 111 does not interfere with the function of the door 104 knob 105. The attachment of the attachment structure 112 to the shell 111 allows the spray structure 102 to target the door 104 knob 105.

Each of the plurality of access doors 113 is a closable port that provides maintenance access to the spray structure 102 and the control circuit 103. Each of the plurality of access doors 113 is used to replace a consumable product that is maintained within the housing 101. Each of the plurality of access doors 113 encloses a consumable product selected from the group consisting of: a) compressed air; b) a disinfectant solution; and, c) a battery 133. The plurality of access doors 113 further comprises a compressed air cartridge 121 access door 141, a disinfectant solution cartridge 122 access door 142, and a battery 133 access door 143.

The compressed air cartridge 121 access door 141 forms the port that provides the access into the spray structure 102 to replace the compressed air cartridge 121 of the spray structure 102. The compressed air cartridge 121 is described elsewhere in this disclosure.

The disinfectant solution cartridge 122 access door 142 forms the port that provides the access into the spray structure 102 to replace the disinfectant solution cartridge 122 of the spray structure 102. The disinfectant solution cartridge 122 is described elsewhere in this disclosure.

The battery 133 access door 143 forms the port that provides the access into the control circuit 103 to replace the battery 133 of the control circuit 103. The battery 133 is described elsewhere in this disclosure.

The spray structure 102 is a mechanical structure. The spray structure 102 is powered using compressed air. The spray structure 102 releases a colloidal suspension formed from the compressed air and a disinfectant solution as a spray that is targeted at the door 104 knob 105. The spray structure 102 comprises a compressed air cartridge 121, a disinfectant solution cartridge 122, a solenoid valve 123, and one or more discharge nozzles 124.

The compressed air cartridge 121 is a cartridge. The compressed air cartridge 121 stores compressed air. The term compressed air is defined elsewhere in this disclosure. The compressed air cartridge 121 is an interchangeable structure. By interchangeable is meant that a first compressed air cartridge 121 can be replaced with a second compressed air cartridge 121 after the compressed air contained in the compressed air cartridge 121 has been exhausted.

The disinfectant solution cartridge 122 is a cartridge. The disinfectant solution cartridge 122 stores a disinfectant solution. The terms disinfectant and solution are defined elsewhere in this disclosure. The disinfectant solution cartridge 122 is an interchangeable structure. By interchangeable is meant that a first disinfectant solution cartridge 122 can be replaced with a second disinfectant solution cartridge 122 after the disinfectant solution contained in the disinfectant solution cartridge 122 has been exhausted.

The solenoid valve 123 is an electrically controlled valve. The control circuit 103 controls the operation of the solenoid valve 123. The solenoid valve 123 forms a fluidic connection between the compressed air cartridge 121 and the disinfectant solution cartridge 122. The solenoid valve 123 controls the flow of compressed air from the compressed air cartridge 121 into the disinfectant solution cartridge 122.

Each of the one or more discharge nozzles 124 is a nozzle that releases the colloidal suspension formed from the compressed air and the disinfectant solution under pressure from the spray structure 102. Each of the one or more discharge nozzles 124 forms a fluidic connection with the disinfectant solution cartridge 122.

As the compressed air enters the disinfectant solution cartridge 122, the pressure of the compressed air mixes with the disinfectant solution to form the colloidal suspension formed from the compressed air and the disinfectant solution. The pressure of the compressed air then transports the colloidal suspension formed from the compressed air and the disinfectant solution to each of the one or more discharge nozzles 124 for discharge.

Each of the one or more discharge nozzles 124 is a spray nozzle that shapes and targets the colloidal suspension formed from the compressed air, and the disinfectant solution as the colloidal suspension formed from the compressed air and the disinfectant solution is discharged from the spray structure 102.

The control circuit 103 is an electric circuit. The control circuit 103 monitors the vicinity of the invention 100 for motion. When the control circuit 103 detects motion in the vicinity of the invention 100, the control circuit 103 releases the colloidal suspension of compressed air and disinfectant solution from the spray structure 102. The control circuit 103 is an independently powered electric circuit. By independently powered is meant that the control circuit 103 can operate without an electrical connection to an external power source. The control circuit 103 comprises a timing circuit 131, a motion sensor 132, and a battery 133. timing circuit 131, the motion sensor 132, the battery 133, and the solenoid valve 123 are electrically interconnected.

The timing circuit 131 is an electric circuit. The timing circuit 131 is defined elsewhere in this disclosure. The timing circuit 131 generates the electric signal used to control the operation of the solenoid valve 123. The timing circuit 131 is triggered by the motion sensor 132. When the motion sensor 132 triggers the timing circuit 131, the timing circuit 131 actuates the solenoid valve 123 to the open position. After the previously determined amount of time has elapsed, the timing circuit 131 actuates the solenoid valve 123 to the closed position. The timing circuit 131 controls the operation of the invention 100 by controlling the flow of the compressed air through the solenoid valve 123.

The motion sensor 132 is a sensor that detects motion within a field of view 151 associated with the motion sensor 132. The motion sensor 132 monitors the vicinity of the motion sensor 132. The motion sensor 132 is defined elsewhere in this disclosure. Upon detecting motion within its field of view 151, the motion sensor 132 generate an electric signal that is transmitted to the timing circuit 131. The electric signal generated by the motion sensor 132 triggers the operation of the timing circuit 131.

The battery 133 is an electrochemical device. The battery 133 converts chemical potential energy into electric energy.

The battery 133 provides the electric energy necessary to operate the timing circuit 131, the motion sensor 132, and the solenoid valve 123.

The following definitions were used in this disclosure:

Aim and Target: As used in this disclosure, the words aim and target are related and are defined together. The word aim means to select the course of the movement of a first object along a path. The target is a second object that lies on the route of the first object such that such that an impact will occur between the first object and the second object.

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Battery: As used in this disclosure, a battery is a chemical device consisting of one or more cells, in which chemical energy is converted into electricity and used as a source of power. Batteries are commonly defined with a positive terminal and a negative terminal.

Cartridge: As used in this disclosure, a cartridge is a device used to contain an object or material in a manner suitable for use by a mechanical device. A cartridge will removably insert into the mechanical device such that the mechanical device can use the object or material as part of the process performed by the mechanical device. The cartridge is removed from the mechanical device once the object or material has been consumed.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Chamber: As used in this disclosure, a chamber is an enclosed or enclosable space within a building.

Clean: As used in this disclosure, the term clean refers to an object without dirt, unwanted markings, or undesirable pathogens. When referring to a surface, the term clean can also refer to removing unwanted objects from the surface. The term cleaning refers to the action of making an object clean.

Cleaning Agent: As used in this disclosure, a cleaning agent is a chemical compound used to remove pathogens, dirt and detritus from a surface.

Cleaning Solution: As used in this disclosure, a cleaning solution is a chemical solution that contains a solvent used to dissolve a cleaning agent.

Closed Position: As used in this disclosure, a closed position refers to a movable barrier structure that is in an orientation that prevents passage through a port or an aperture. The closed position is often referred to as an object being "closed." Always use orientation.

Colloidal Suspension: As used in this disclosure, a colloidal suspension, or colloid for short, is a heterogeneous mixture of solute particles dissolved in a solvent. The colloidal suspension is referred to as heterogeneous because the distribution of the solute particles is not uniform through the solvent, usually because of the relatively large size of the particles. When the solvent is a gas, a colloidal suspension is often referred to as an aerosol.

Compressed Air: In this disclosure, compressed air means air that has been compressed to a pressure greater than normal temperature and pressure.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Control Circuit: As used in this disclosure, a control circuit is an electrical circuit that manages and regulates the behavior or operation of a device.

Correspond: As used in this disclosure, the term correspond is used as a comparison between two or more objects wherein one or more properties shared by the two or more objects match, agree, or align within acceptable manufacturing tolerances.

Course: As used in this disclosure, a course refers to the direction, and changes to the direction, that are required to travel from a starting point to a destination point.

Disinfectant: As used in this disclosure, a disinfectant is a chemical that destroys or inhibits the biochemical activities of pathogenic microorganisms.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Door: As used in this disclosure, a door is a movable or removable barrier that is attached to a chamber for the purpose of allowing or preventing access through an aperture into the chamber.

External Power Source: As used in this disclosure, an external power source is a source of the energy that is externally provided to enable the operation of the present disclosure. Examples of external power sources include, but are not limited to, electrical power sources and compressed air sources.

Field of View: As used in this disclosure, a field of view refers to one or more angles which delimits an area from which electromagnetic radiation will be sensed by a person or an image sensor.

Flow: As used in this disclosure, a flow refers to the passage of a fluid past a fixed point. This definition considers bulk solid materials as capable of flow.

Fluid: As used in this disclosure, a fluid refers to a state of matter wherein the matter is capable of flow and takes the shape of a container it is placed within. The term fluid commonly refers to a liquid or a gas.

Fluidic Circuit: As used in this disclosure, a fluidic circuit is a closed loop path through which a fluid flows. The closed loop will generally initiate and terminate at reservoir.

Fluidic Connection: As used in this disclosure, a fluidic connection refers to a tubular structure that transports a fluid from a first object to a second object. Methods to design and use a fluidic connections are well-known and documented in the mechanical, chemical, and plumbing arts.

Form Factor: As used in this disclosure, the term form factor refers to the size and shape of an object.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Grip: As used in this disclosure, a grip is an accommodation formed on or within an object that allows the object to be grasped or manipulated by a hand.

Handle: As used in this disclosure, a handle is an object by which a tool, object, or door is held or manipulated with the hand.

Housing: As used in this disclosure, a housing is a rigid structure that encloses and protects one or more devices.

Impact: As used in this disclosure, an impact refers to an exchange of momentum between two objects over a duration. An impact often refers to a collision between two objects.

Interchangeable: As used in this disclosure, interchangeable refers to the ability to remove and replace an element of a structure. For example, if a first object that is attached to a structure can be removed and replaced with a second object selected from a plurality of compatible objects than the first object is said to be replaceable with both: 1) the second object; and, 2) each of the elements of compatible objects. Term interchangeable is commonly associated with tools. Interchangeable objects are often used to change the function or the performance characteristics of a tool.

Latch: As used in this disclosure, a latch is a fastening or locking mechanism commonly used to secure a lid, a door, or, a gate.

Liquid: As used in this disclosure, a liquid refers to a state (phase) of matter that is fluid and that maintains, for a given pressure, a fixed volume that is independent of the volume of the container.

Maintenance: As used in this disclosure, maintenance refers to activities intended to preserve the operating effectiveness of a device from reduction that occurs through the normal and intended use of the device.

Microorganism: As used in this disclosure, a microorganism is an organism too small to be viewed by the unaided eye. Microorganisms are typically single celled organisms such as bacteria, yeast, viruses, protozoa, fungi and algae. A pathogen refers to a microorganism that has the potential to cause illness or disease.

Momentum: As used in this disclosure, momentum is a measured quantity associated with the mass of a moving object. The momentum of the object equals the mass of the object multiplied by the velocity of the object. The exchange of momentum between two objects is a conserved quantity meaning that the sum of the momentums of the two objects before an exchange of momentum equals the sum of the momentums of the two objects after the exchange.

Motion Sensor: As used in this disclosure, a motion sensor refers to a commercially available sensor that generates an electrical signal should the motion sensor detect movement within its field of view.

Negative Space: As used in this disclosure, negative space is a method of defining an object through the use of open or empty space as the definition of the object itself, or, through the use of open or empty space to describe the boundaries of an object.

Non-Polar Molecule: As used in this disclosure, a non-polar molecule refers to a molecular structure that: a) is electrically neutral; and, b) has a uniform spatial distribution of the electrons within the molecule.

Nozzle: As used in this disclosure, a nozzle is a device that receives fluid under pressure and releases the fluid in a controlled manner into an environment.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Open Position: As used in this disclosure, an open position refers to a movable barrier structure that is in an orientation that allows passage through a port or an aperture. The open position is often referred to as an object being "open."

Orientation: As used in this disclosure, orientation refers to the positioning of a first object relative to: 1) a second object; or, 2) a fixed position, location, or direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan is are open.

Path: As used in this structure, a path is a marked or identified route along which an individual or object can travel. A path is often formed as a track, a road or a trail.

Perimeter: As used in this disclosure, a perimeter is one or more curved or straight lines that bounds an enclosed area on a plane or surface. The perimeter of a circle is commonly referred to as a circumference.

Phase: As used in this disclosure, phase refers to the state of the form of matter. The common states of matter are solid, liquid, gas, and plasma.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Route: As used in this disclosure, a route refers to the course that is taken to travel from a starting point to a destination point.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Shell: As used in this disclosure, a shell is a structure that forms an outer covering intended to contain an object. Shells are often, but not necessarily, rigid or semi-rigid structures that are intended to protect the object contained within it.

Solenoid: As used in this disclosure, a solenoid is a cylindrical coil of electrical wire that generates a magnetic field that can be used to mechanically move a shaft made of a magnetic core.

Solenoid Valve: As used in this disclosure, a solenoid valve is an electromechanically controlled valve that is used to control fluid or gas flow. A two port solenoid valve opens or closes to fluid flow through the valve portion of the solenoid valve. A three port solenoid valve switched fluid or gas flow between a first port and a second port to either feed or be fed from a third port. A solenoid valve comprises a coil and a valve. The coil forms the solenoid that opens and closes the solenoid valve. The solenoid valve is a valve that opens and closes to control the fluid flow.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Spray: As used in this disclosure, a spray is a plurality of liquid drops dispersed in a gas.

Spray Nozzle: As used in this disclosure, a spray nozzle is a device that receives liquid under pressure and disperses that liquid into the atmosphere as a spray.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry. The "555" timing circuit is a well-known, documented, and commercially available timing circuit.

Timing Device: As used in this disclosure, a timing device is an automatic mechanism for activating or deactivating a device at a specific time or after a specific period of time. This disclosure assumes that the logic module is provisioned with a timing circuit that can be used as a timing device. A timing device that activates an audible alarm is often referred to as a timer.

Trigger: As used in this disclosure, a trigger is a subcomponent of a mechanism that: a) is used to activate a mechanism; and, b) returns to its original position (or state) after the mechanism has been activated.

Vicinity: As used in this disclosure, vicinity refers to the space immediately, or closely, surrounding a first object. A second object is said to be in the vicinity of the first object.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A self-sanitizing door handle comprising
a housing, a spray structure, and a control circuit;
wherein the housing contains the spray structure and the control circuit;
wherein the self-sanitizing door handle is for use with a door knob of a door;
wherein the self-sanitizing door handle is incorporated into the door knob;
wherein the spray structure disinfects the door knob by discharging a spray disinfecting solution onto the door knob;
wherein the control circuit controls the operation of the spray structures;
wherein the control circuit: a) detects motion in the vicinity of the self-sanitizing door handle; and, b) discharges the disinfecting solution onto the door knob when this motion is detected;
wherein the housing comprises a shell, an attachment structure, and a plurality of access doors;
wherein the attachment structure attaches the shell to the door knob;
wherein the plurality of access doors are formed in the shell.

2. The self-sanitizing door handle according to claim 1 wherein the housing is a rigid structure.

3. The self-sanitizing door handle according to claim 2
wherein the spray structure is a mechanical structure;
wherein the spray structure is powered using compressed air;
wherein the spray structure releases a colloidal suspension formed from the compressed air and a disinfectant solution as a spray that is targeted at the door knob.

4. The self-sanitizing door handle according to claim 3
wherein the spray structure comprises a compressed air cartridge, a disinfectant solution cartridge, a solenoid valve, and one or more discharge nozzles;
wherein the compressed air cartridge is a cartridge;
wherein the compressed air cartridge stores compressed air;
wherein the disinfectant solution cartridge is a cartridge;
wherein the disinfectant solution cartridge stores a disinfectant solution;
wherein the solenoid valve forms a fluidic connection between the compressed air cartridge and the disinfectant solution cartridge;
wherein each of the one or more discharge nozzles forms a fluidic connection with the disinfectant solution cartridge.

5. The self-sanitizing door handle according to claim 4
wherein the control circuit is an electric circuit;
wherein the control circuit monitors the vicinity of the self-sanitizing door handle for motion;
wherein when the control circuit detects motion in the vicinity of the self-sanitizing door handle, the control circuit releases the colloidal suspension of compressed air and disinfectant solution from the spray structure.

6. The self-sanitizing door handle according to claim 5
wherein the control circuit is an independently powered electric circuit;
wherein by independently powered is meant that the control circuit can operate without an electrical connection to an external power source.

7. The self-sanitizing door handle according to claim 6
wherein the control circuit comprises a timing circuit, a motion sensor, and a battery;
wherein timing circuit, the motion sensor, the battery, and the solenoid valve are electrically interconnected.

8. The self-sanitizing door handle according to claim 7
wherein the shell is formed as a disk;
wherein the shell is a rigid structure;
wherein the shell contains the spray structure and the control circuit.

9. The self-sanitizing door handle according to claim 8
wherein each of the plurality of access doors is a closable port that provides maintenance access to the spray structure and the control circuit;
wherein each of the plurality of access doors is used to enclose a consumable product that is maintained within the housing;
wherein each of the plurality of access doors encloses a consumable product selected from the group consisting of: a) compressed air; b) a disinfectant solution; and, c) the battery.

10. The self-sanitizing door handle according to claim 9
wherein the plurality of access doors further comprises a compressed air cartridge access door, a disinfectant solution cartridge access door, and a battery access door;
wherein the compressed air cartridge access door forms the port that provides the access into the spray structure to replace the compressed air cartridge of the spray structure;
wherein the disinfectant solution cartridge access door forms the port that provides the access into the spray structure to replace the disinfectant solution cartridge of the spray structure;
wherein the battery access door forms the port that provides the access into the control circuit to replace the battery of the control circuit.

11. The self-sanitizing door handle according to claim 10
wherein the compressed air cartridge is an interchangeable structure;
wherein by interchangeable is meant that a first compressed air cartridge can be replaced with a second compressed air cartridge after the compressed air contained in the compressed air cartridge has been exhausted;
wherein the disinfectant solution cartridge is an interchangeable structure;
wherein by interchangeable is meant that a first disinfectant solution cartridge can be replaced with a second disinfectant solution cartridge after the disinfectant solution contained in the disinfectant solution cartridge has been exhausted.

12. The self-sanitizing door handle according to claim 11
wherein the solenoid valve is an electrically controlled valve;
wherein the control circuit controls the operation of the solenoid valve;
wherein the solenoid valve controls the flow of compressed air from the compressed air cartridge into the disinfectant solution cartridge.

13. The self-sanitizing door handle according to claim 12
wherein each of the one or more discharge nozzles is a nozzle that releases the colloidal suspension formed from the compressed air and the disinfectant solution under pressure from the spray structure;
wherein as the compressed air enters the disinfectant solution cartridge, the pressure of the compressed air mixes with the disinfectant solution to form the colloidal suspension formed from the compressed air and the disinfectant solution.

14. The self-sanitizing door handle according to claim 13 wherein each of the one or more discharge nozzles is a spray nozzle that shapes and targets the colloidal suspension formed from the compressed air and the disinfectant solution as the colloidal suspension formed from the compressed air and the disinfectant solution is discharged from the spray structure.

15. The self-sanitizing door handle according to claim 14
wherein the timing circuit is an electric circuit;
wherein the timing circuit generates the electric signal used to control the operation of the solenoid valve.

16. The self-sanitizing door handle according to claim 15
wherein the timing circuit is triggered by the motion sensor;
wherein when the motion sensor triggers the timing circuit, the timing circuit actuates the solenoid valve to the open position;
wherein after the previously determined amount of time has elapsed, the timing circuit actuates the solenoid valve to the closed position;
wherein the timing circuit controls the operation of the self-sanitizing door handle by controlling the flow of the compressed air through the solenoid valve.

17. The self-sanitizing door handle according to claim 16
wherein the motion sensor is a sensor that detects motion within a field of view associated with the motion sensor;

wherein the motion sensor monitors the vicinity of the motion sensor;
wherein upon detecting motion within its field of view, the motion sensor generates an electric signal that is transmitted to the timing circuit;
wherein the electric signal generated by the motion sensor triggers the operation of the timing circuit.

18. The self-sanitizing door handle according to claim 17 wherein the battery is an electrochemical device;
wherein the battery converts chemical potential energy into electric energy;
wherein the battery provides the electric energy necessary to operate the timing circuit, the motion sensor, and the solenoid valve.

\* \* \* \* \*